United States Patent [19]

Matsuda et al.

[11] Patent Number: 4,564,615
[45] Date of Patent: Jan. 14, 1986

[54] IMMUNOACTIVATOR

[75] Inventors: Hideaki Matsuda, Abiko; Ryohta Tatezaki, Yachiyo; Hiroyuki Mizuno, Shisui; Tatsuhiko Katori, Tone, all of Japan

[73] Assignee: SS Pharmaceutical Co., Ltd., Tokyo, Japan

[21] Appl. No.: 441,177

[22] Filed: Nov. 12, 1982

Related U.S. Application Data

[63] Continuation of Ser. No. 331,760, Dec. 17, 1981, abandoned.

[30] Foreign Application Priority Data

Dec. 26, 1980 [JP] Japan ................................ 55-186145
Oct. 21, 1981 [JP] Japan ................................ 56-168199

[51] Int. Cl.[4] ........................................... A61K 31/535
[52] U.S. Cl. .................................. 514/231; 514/825; 514/885; 514/892
[58] Field of Search .................... 424/248.51; 514/231

[56] References Cited
PUBLICATIONS

Chem. Abst. 88:50879f, 1978.

Primary Examiner—Allen J. Robinson
Assistant Examiner—John W. Rollins, Jr.
Attorney, Agent, or Firm—Oblon, Fisher, Spivak, McClelland & Maier

[57] ABSTRACT

An immunoactivator comprising an effective amount of a thiazolobenzoxazine derivative of the formula, or its salt

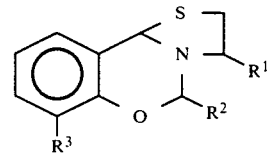

wherein $R^1$ represents a hydrogen atom, carboxyl group or lower alkoxycarbonyl group, $R^2$ represents a substituted or unsubstituted phenyl group, lower alkyl group or furyl group, and $R^3$ represents a hydrogen atom or lower alkoxy group.

8 Claims, 5 Drawing Figures

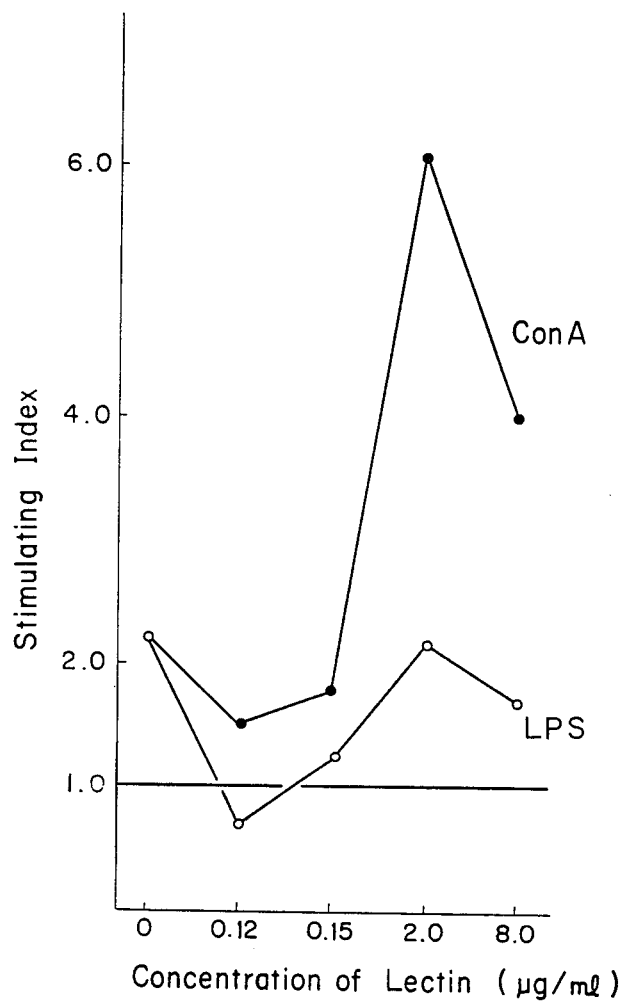

IMMUNOACTIVATOR

This is a continuation of application Ser. No. 331,760, filed Dec. 17, 1981, abandoned.

BACKGROUND OF THE INVENTION

1. Field of the Invention

This invention relates to a medicine and more particularly to a novel immunoactivator which is very effective against various diseases which will cause immunological abnormality or deficiency or which will cause abnormality or deficiency in myeloid cells or differentiation thereof.

2. Description of the Prior Art

We have proposed in our Japanese Patent Publication No. 56-6433 thiazolobenzoxazine derivatives of the general formula (I)

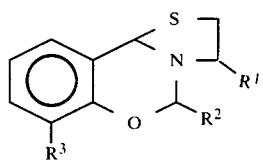
(I)

in which $R^1$ represents a hydrogen atom, carboxyl group or lower alkoxycarbonyl group, $R^2$ represents a substituted or unsubstituted phenyl group, lower alkyl group or furyl group, and $R^3$ represents a hydrogen atom or lower alkoxy group. It has been found that these compounds show an anti-inflammatory and analgetic action.

A further study on these compounds has revealed that these compounds have, aside from the above-mentioned pharmaceutical action, a hitherto unknown immunoactivating action and show very low toxicity.

SUMMARY OF THE INVENTION

Accordingly, an object of the present invention is to provide a novel and excellent immunoactivator.

The above object can be achieved, according to the invention, by an immunoactivator which comprises an effective amount of a thiazolobenzoxazine derivative represented by the general formula (I), or its salt

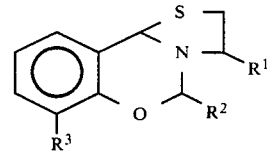
(I)

in which $R^1$, $R^2$ and $R^3$ have the same meanings as defined above.

The present invention will become apparent from the following description taken in conjunction with the accompanying drawings.

BRIEF DESCRIPTION OF THE DRAWINGS

FIG. 4 is a graph showing a comparison between Con A and LPS in respect of the stimulating factor obtained from FIGS. 3(a) and 3(b).

DETAILED DESCRIPTION AND EMBODIMENTS OF THE INVENTION

Figure 1:
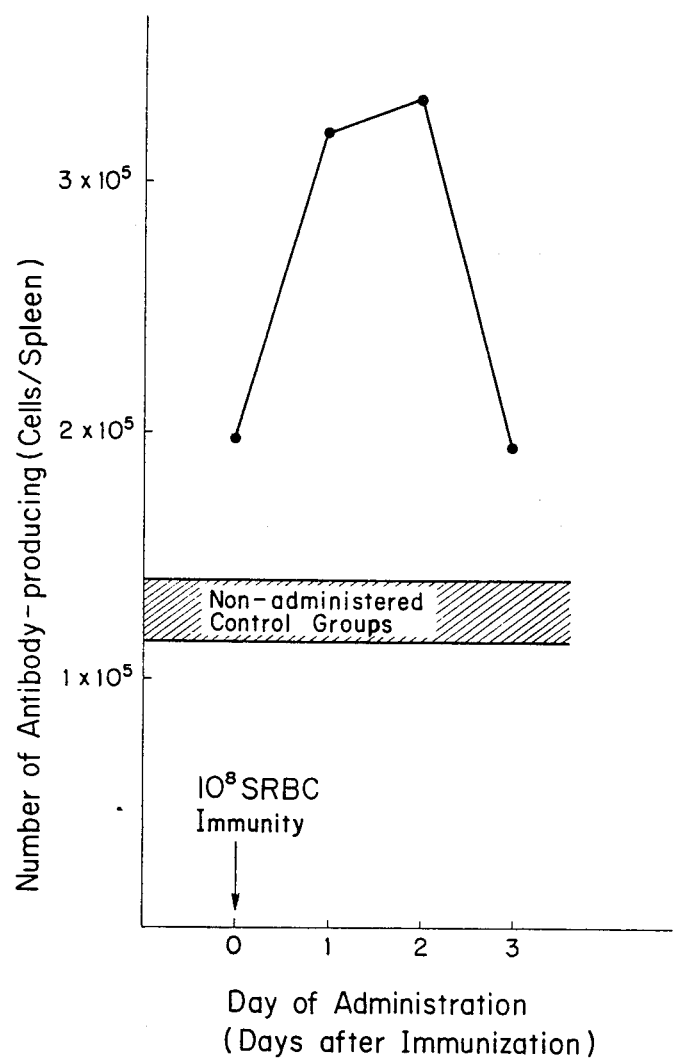
FIG. 1 is a graph showing a relation between the time of administration of a compound according to the invention and the number of antibody-producing cells.

In the formula (I), when $R^2$ represents a substituted phenyl group, the substituent represents a halogen atom, hydroxyl group, carboxyl group, lower alkoxy group, methylenedioxy group, aldehyde group, amino group such as dimethylamino group, nitro group or group of the formula in which $R^1$ and $R^3$ have the same meanings as defined hereinbefore, respectively. The phenyl group is substituted with one or more of these groups.

Typical examples of the compound of the formula (I) used as an effective component of the immunoactivator according to the invention are enumerated in Table 1.

Any of these compounds can be readily prepared according to the method described in the aforeindicated Patent Publication No. 56-6433.

TABLE 1

| Compound No. | $R^1$ | $R^2$ | $R^5$ | Melting Point (°C.) |
|---|---|---|---|---|
| 1 | H | —⟨phenyl⟩ | H | 153–155 |

TABLE 1-continued
| Compound No. | R¹ | R² | R⁵ | Melting Point (°C.) |
|---|---|---|---|---|
| 2 | H | 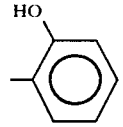 | H | 128–130 |
| 3 | H | 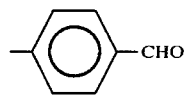 | H | 142–143 |
| 4 | H | 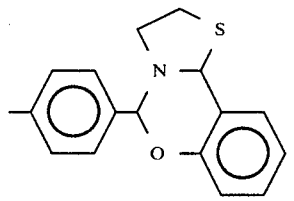 | H | 254–260 (decomposed) |
| 5 | H | 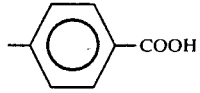 | H | 173–176 (decomposed) |
| 6 | H | 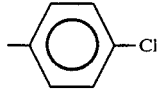 | H | 120.5–122.5 |
| 7 | H | 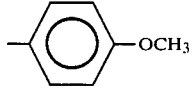 | H | 132.5–134.5 |
| 8 | H | 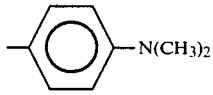 | H | 185–187.5 |
| 9 | H | 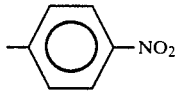 | H | 169.5–171.5 |
| 10 | H | 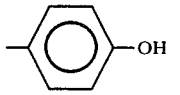 | H | 147–149 |
| 11 | H | 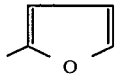 | H | 98–100 |
| 12 | H | 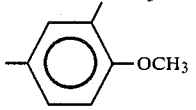 | H | 164–166 |
| 13 | H | 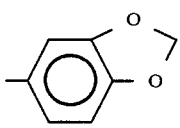 | H | 196–198 |

TABLE 1-continued
| Compound No. | R¹ | R² | R⁵ | Melting Point (°C.) |
|---|---|---|---|---|
| 14 | H | 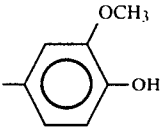 | H | 172–173 |
| 15 | —COOCH₃ | 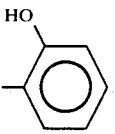 | H | 139–140.5 |
| 16 | —COOCH₃ | 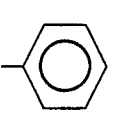 | H | 128.5–130 |
| 17 | —COOCH₃ | 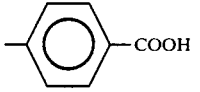 | H | 158–161 |
| 18 | —COOCH₃ | 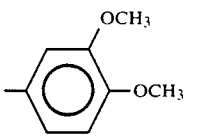 | H | 149.5–151.5 |
| 19 | —COOCH₃ | 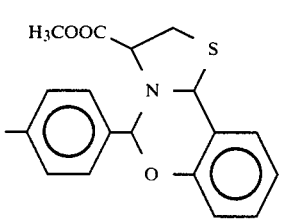 | H | 195–199 (decomposed) |
| 20 | —COOCH₃ | 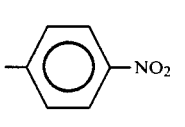 | H | 136–138 |
| 21 | —COOCH₃ | 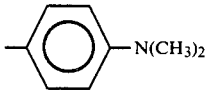 | H | 181–184 |
| 22 | —COOCH₃ | 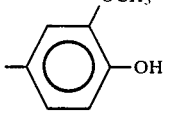 | H | 136.5–138 |
| 23 | H | 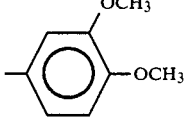 | —OCH₃ | 190.5–191.5 |
| 24 | H | 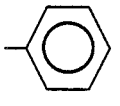 | —OCH₃ | 149.5–151 |

TABLE 1-continued

| Compound No. | R¹ | R² | R⁵ | Melting Point (°C.) |
|---|---|---|---|---|
| 25 | H | —C₆H₄—OCH₃ (para) | —OCH₃ | 165–167 |
| 26 | H | —C₆H₄—Cl (para) | —OCH₃ | 150–151.5 |
| 27 | H | —C₆H₄—NO₂ (para) | —OCH₃ | 188–190 |
| 28 | H | 3,4-methylenedioxyphenyl | —OCH₃ | 175.5–178 |
| 29 | H | —C₆H₄—N(CH₃)₂ (para) | —OCH₃ | 168.5–172 |
| 30 | H | 2-furyl | —OCH₃ | 148–150 |
| 31 | H | —C₆H₄—CHO (para) | —OCH₃ | 164–168 |
| 32 | H | (fused thiazolidine-benzoxazine with H₃CO substituent) | —OCH₃ | 246–249 (decomposed) |
| 33 | H | —C₂H₅ | —OCH₃ | 97–99 |

The compounds enumerated in Table 1 can be converted into corresponding inorganic or organic salts by a usual manner. For this purpose, there are preferably used acids such as hydrochloric acid, sulfuric acid, nitric acid, fumaric acid and maleic acid. As regards the compounds having a carboxyl group therein such as those of Nos. 5 and 17, they can be converted into sodium or potassium salt.

These salts remarkably increase in solubility in water and can suitably be administered as aqueous solution.

The immunoactivating effects of a typical compound or compounds used in the immunoactivator according to the invention are described.

1. Action on Antibody Production
  (1) IgM Antibody Producing Action
  (i) Groups of CDF₁ mice (male, 10 weeks old), each group consisting of 5 mice, were each venously injected with $1 \times 10^8$ sheep red blood cells as an antigen for immunization. At the same time, the compound of No. 3 in Table 1 was orally dosed to the mice in amounts ranging 400 μg/mouse–0.4 μg/mouse. Four days after the administration, the number of the antibody-producing cells in the spleen cells of each mouse was calculated according to the methods of Jerne et al.* and Cuningham et al.** to check the antibody-producing activity of the compound. The results are shown in Table 2. As will be apparent from the table, the administration of the compound in amounts ranging 100–400 μg/mouse contributes to potentiate the antibody production.

*Jerne, N. K.; A. A. Nordin & C. Henry: The agar plague technique for recognizing antibody-producing cells in Cell-bound antibodies, pp. 109–122. Wistar Institute Press, Philadelphia, 1963.
**Cunningham, A. J. & A. Szenberg: Immunology 14: 599–600, 1968.

TABLE 2

| Tested Compound (μg/mouse) | Number of Antibody-producing cells/spleen (average value) | T/C (%)[1] |
|---|---|---|
| 400 | 308,610 | 148 |
| 100 | 398,520 | 191 |
| 25 | 176,040 | 84 |
| 6.2 | 189,216 | 91 |
| 1.6 | 217,890 | 104 |
| 0.4 | 221,130 | 106 |
| 0 (control group) | 208,980 | 100 |

[1]T/C (%) = $\frac{\text{Number of antibody-producing cells of test groups}}{\text{Number of antibody-producing cells of control group}} \times 100$ (ii) Groups of $CDF_1$ mice (male, 12 weeks old), each group consisting of 5 mice, were each venously injected with $1 \times 10^8$ sheep red blood cells for immunization. The thus injected mice were each orally dosed with a compound of the invention (compound No. 3 in Table 1) at the same day as of the injection (0 day), 1 day, 2 days and 3 days after the injection in an amount of 100 μg/mouse. Four days after the immunization, the number of antibody-producing cells in the spleen cells of each mouse of each group was determined. The results are shown in FIG. 1.

From these results, it becomes apparent that the administered groups of the compound of the invention, whichever they may, including the group administered at the day of the immunization and groups administered at an days after the immunization show increased numbers of antibody-producing cells over the non-administered groups thereby potentiating the antibody production. Further, the compound of the invention shows a maximum potentiation when administered 1-2 days after the stimulation of antigen.

(2) Antibody-producing Action Based on Cell Culture

Figure 2:
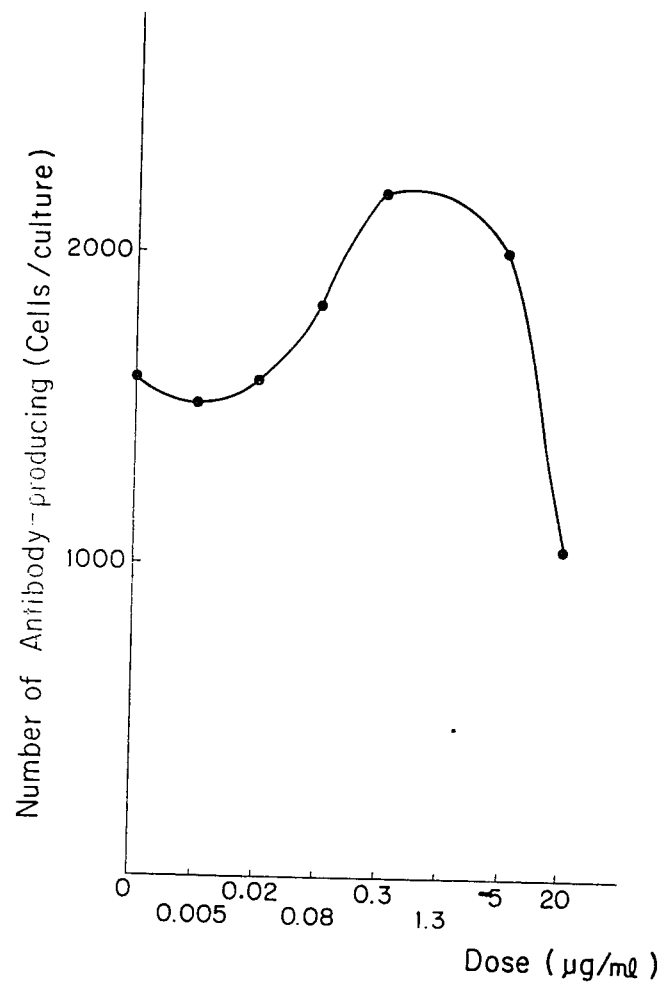
FIG. 2 is a graph showing a relation between the dose of a compound of the invention and the number of antibody-producing cells.

The action of a compound of the invention on the antibody-producing system with respect to sheep red blood cells was investigated on the basis of the mouse's spleen cell culture according to the Mishell & Dutton's method* and its modification**. The test was conducted as follows: To cultured mouse's spleen cells was added 0.005 μg-20 μg/ml of a compound of the invention (Compound No. 3 in Table 1) and the cells were cultured together with $1 \times 10^6$ sheep red blood cells in the presence of 5% $CO_2$ at 37° C., and, after 4 days, the number of antibody-producing cells in the individual cultured spleen cells was calculated according to the method of Cunningham et al. The results are shown in FIG. 2, revealing that significant potentiation of the antibody-producing action was observed in the range of 0.3-5μg/ml.

*Mishell, R. I. & R. W. Dutton: J. Exp. Med. 126, 423–442, 1967.
**Click, R. E., L. Benck & B. J. Alter: Cellular Immunol. 3: 156–160, 1972.

2. Action on Delayed-Type Hypersensitivity

In order to evaluate an action of compounds of the invention on cellular immunity which plays the most important role on the protection reaction against viral infection, the action was investigated according to the method of Lagrange et al.* using as an index the effect on the delayed-type hypersensitivity in which sheep red blood cells were provided as antigen**.

*Lagrange, P. H., G. B. Mackaness & T. E. Miller: J. Exp. Med., 139: 528–542, 1974.
**Ishizuka, M. T. Matsuda, N. Kanbayashi, S. Fukasawa, T. Takeuchi, T. Aoyagi & H. Umezawa: J. Antibiotics 33: 642–652, 1980.

That is, groups of $CDF_1$ mice (male, 12 weeks old), each group consisting of 5 mice, were each immunized by being subcutaneously injected with $10^8$ sheep red blood cells at the soles of right hind leg and were simultaneously orally dosed with 4 μg-1 mg/mouse of a compound of the invention (compound No. 3 in Table 1). Four days after the administration, $10^8$ sheep red blood cells were subcutaneously injected into each mouse at the sole of the left hind leg, thereby causing the reaction. 24 hours after the injection, the thickness of the foot sole was measured and degrees of swelling of the soles were compared with one another to judge the action.

The results are as shown in Table 3 and reveal that the administered groups of the inventive compound in amounts ranging from 4 μg to 1 mg 1 mouse show more pronounced potentiation on the delayed-type hypersensitivity than the non-administered control groups and thus it is apparent that the present compound has the potentiating action on the cellular immunity.

TABLE 3

| Dose (μg/mouse) | Thickness of Sole Swelling ($\times$ 0.1 mm, ± S.D.) | T/C %[1] |
|---|---|---|
| 1000 | 13.3 ± 1.3 | 208 |
| 250 | 12.7 ± 1.7 | 198 |
| 62 | 11.6 ± 1.6 | 181 |
| 16 | 9.6 ± 1.0 | 150 |
| 4 | 14.8 ± 1.1 | 231 |
| 0 | 6.4 ± 0.9 | 100 |

[1]T/C (%) = $\frac{\text{Thickness of Sole Swelling of Administered Groups}}{\text{Thickness of Sole Swelling of Non-administered Groups}} \times 100$ 3. Action on Phagocytosis of Peritoneal Macrophage The action of the inventive compound on the phagocytosis of macrophage was investigated.

$CDF_1$ mice (female, 8 weeks old) were each peritoneally injected with 2 ml of a thioglycolate medium to allow the peritoneal macrophages to be released. Four days after the injection, a compound of the invention (Compound No. 3 in Table 1) was peritoneally injected into each mouse in an amount ranging from 1 μg to 1 mg/mouse. 18 hours after the injection, the mice of each group was peritoneally washed with the Dulbecco phosphate buffer solution to collect the peritoneal macrophages, which were then suspended in a serum-free Dulbecco phosphate buffer solution and the suspension was placed in plastic petri dishes, followed by keeping in a 5% carbonic acid gas culture container at 37° C. for 2 hours to obtain adhesive cells. To the respective petri dishes containing the adhesive cells was added a solution of a germ Saccharomyces cervisiae. After having kept the temperature for 30 minutes, the germ solution was removed, followed by culturing 4 hours, washing, and subjecting to the Giemsa staining. Then, the number of cells phagocytizing the germ were counted under microscope to determine the effect of the compound*.

*M. Ishizuka; S. Fukasawa, T. Masuda, J. Sato, N. Kanbayashi, T. Takeuchi & H. Umezawa; J. Antibiotics 32: 330–339, 1980.

The results are shown in Table 4, from which it will be seen that the administration of the compound in amounts of 1 μg-100 μg/mouse contributes to improve the phagocytosis of macrophage.

TABLE 4

| Dose (μg/mouse) | T/C (%) |
|---|---|
| 1 | 127 |
| 10 | 133 |
| 100 | 137 |

TABLE 4-continued

| Dose (μg/mouse) | T/C (%) |
|---|---|
| 1000 | 115 |

4. Action on Blastogenesis of Splenic Cells (1) The splenic cells of $CDF_1$ mice (female, 10 weeks old) were collected and were cultured in a 10% foetal calf serum-added RPMI 1640 medium adding a lectin such as Concanavalin A (Con A) or Lipopolysaccharide (LPS) and a compound of the invention (Compound No. 3 in Table 1), and the blasting effect was determined using as an index incorporation of $^3$H-thymidine into the cultured splenic cells. The results are shown in Table 5.

TABLE 5

| Amount | Lectin | | |
|---|---|---|---|
| (μg/ml) | No | Con A (0.5 μg/ml) | LSP (0.5 μ/ml) |
| 20 | 105 | 1267 | 665 |
| 10 | 811 | 9982 | 4007 |
| 5 | 148 | 2131 | 1068 |
| 0 | 204 | 3556 | 1336 |

(In the table, the unit for the three columns as viewed from the right is cpm/culture.)

As a results, the addition of 10 μg/ml of the compound of the invention serves to accelerate the blasting reaction caused by the lectins including either of Con A and LPS. In addition, in the case of the culture free of any lectin, the inventive compound more or less expedites the incorporation of $^3$H-thymidine into the splenic cells.

Figure 3A:
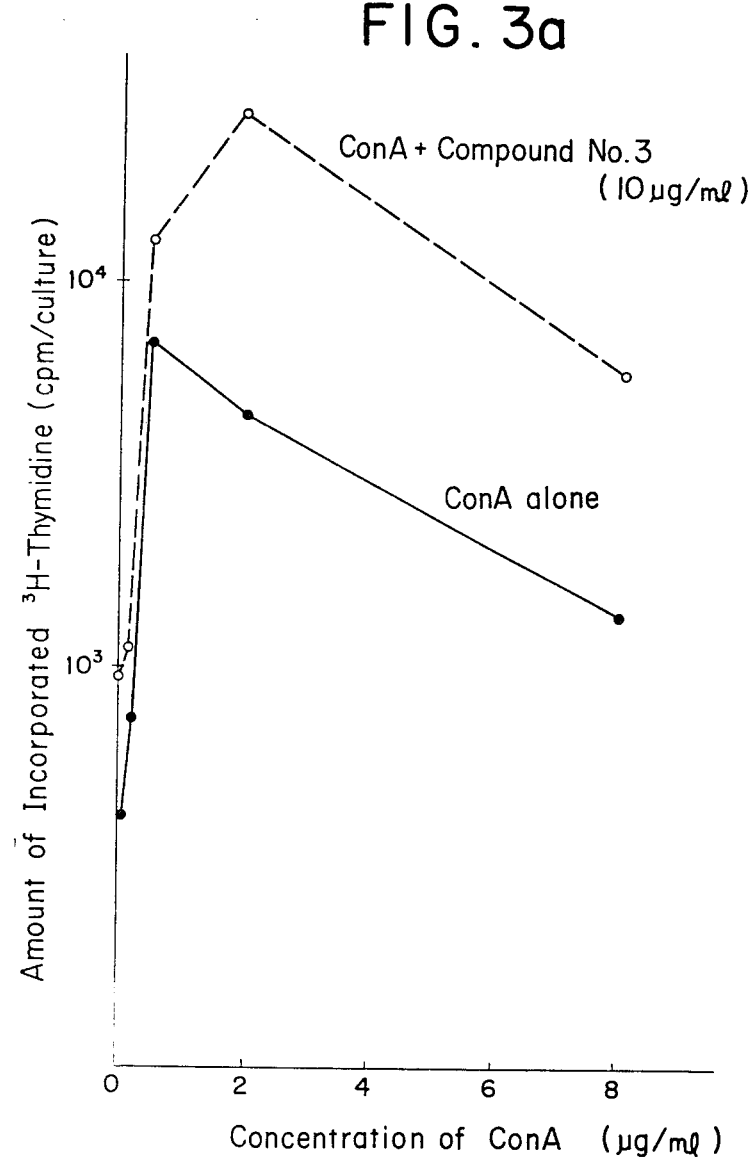
FIGS. 3(a) and 3(b) are graphs showing a potentiation effect of an inventive compound on the mouse's splenic cell blasting reaction.
Figure 3B:
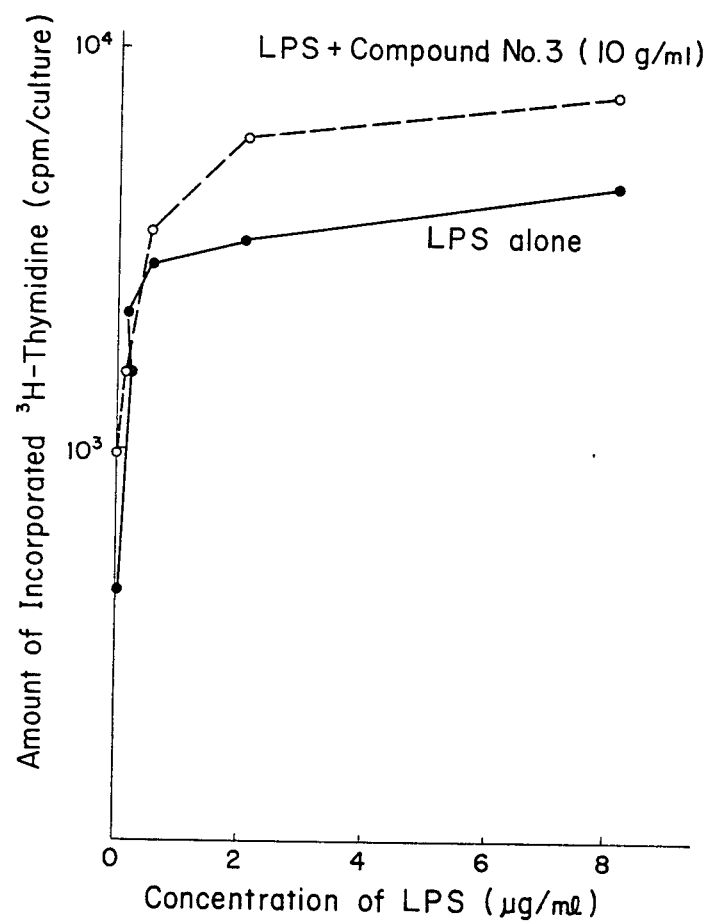

(2) The splenic cells of the mouse to which had been added different amounts of Con A or LPS and then 10 μg/ml of the inventive compound (Compound No. 3 in Table 3) were cultured to know the effect on the blasting reaction. The results are shown in FIGS. 3a and 3b. The compound of the invention serves to potentiate the blasting reaction when the amount of the Con A or LSP is in the range of 0.5–8 μg/ml. Further, in order to know whichever lectin is greatly influenced by the compound of the invention for the potentiation, a stimulatory index* was calculated from the results of FIGS. 3a and 3b. As shown in FIG. 4, the Con A which is T-cell mitogen is more greatly acted with the compound than the LPS which is β-cell mitogen.

$$*\text{Stimulatory index} = \frac{\text{cpm of }^3\text{H—thymidine incorporated into cells cultured in medium in which lectin and inventive compound are added}}{\text{cpm of }^3\text{H—thymidine incorporated into cells cultured in medium added with lectin alone}}$$

5. Action on Production of Glanulocytic Macrophage Colony (CFU-C) at Myeloid Cell Culture In accordance with the methods of Metcalf* and Stanley et al., the myeloid cells of mouse were cultured in soft agar to which a colony stimulating factor (CSF)* and different amounts of a compound of the invention (Compound No. 3 in Table 1) to investigate the action on the glanulocytic macrophage colony. The results shown in Table 6 reveals that the addition of the inventive compound in amounts ranging from 0.1 to 1 μg/ml contributes to remarkably potentiate the production of CFU-C.

*Metcalf, D: Immunology 21: 427–436, 1971.
**Stanley, E. R., M. Cifone, P. M. Heard & V. Deffendi: J. Exp. Med. 143: 631–647, 1976.
***The mouse serum obtained 6 hours after venous injection of 5 μg of LPS into $CDF_1$ mouse was added in an amount of 0.0125 ml as the colony stimulating factor.

TABLE 6

| Amount of the Inventive Compound (μg/ml) | Number of CFU-C (±S.D.) | T/C (%) |
|---|---|---|
| 0 | 136 ± 5 | — |
| 0.001 | 140 ± 6 | 103 |
| 0.01 | 156 ± 9 | 115 |
| 0.1 | 189 ± 3 | 139 |
| 1 | 221 ± 6 | 163 |
| 10 | 144 ± 16 | 106 |

$$T/C\ (\%) = \frac{\text{Number of CFU-C when the inventive compound was added}}{\text{Number of CFU-C when the inventive compound was not added}} \times 100$$

Acute Toxicity

Typical compounds used in the immunoactivator according to the invention were each suspended in physiological salt solution and intraperitoneally administered into groups of male mice, each consisting of 5 mice, followed by breeding and observing for 7 days. As a result it was found that, at the dose of 500 mg/kg, all the mice survived without involving any abnormal changes. Accordingly, as shown in Table 7, $LD_{50}$ of all the compounds is over 500 mg/kg with the toxicity being very small.

TABLE 7

| Compound No. | Acute Toxicity ($LD_{50}$) |
|---|---|
| 1 | 500 μg/kg |
| 2 | μ |
| 3 | μ |
| 5 | μ |
| 6 | μ |
| 7 | μ |
| 8 | μ |
| 11 | μ |
| 14 | μ |
| 15 | μ |
| 17 | μ |
| 21 | μ |
| 24 | μ |
| 29 | μ |
| 31 | μ |
| 33 | μ |

Then, the manner and amount of administration of the immunoactivator according to the invention is described.

The manner of administration includes oral administration in the form of tablets, capsules, granules, syrup and the like, and parenteral administration such as subcutaneous injection, intramuscular injection, intravenous injection, drop by mixing with infusion and suppository.

The amount of administration may vary depending on the manner of administration and is suitably in the range of 0.01–500 mg/kg for the oral administration, and 0.005–250 mg/kg for the parenteral administration.

Oral preparations can be made by usual manner of manufacture. That is, tablets, capsules and granules can be made by formulating the compound in combination with excipients such as starch, lactose, mannitol and the like, binders such as sodium carboxymethyl cellulose, hydroxy propyl cellulose and the like, disintegrators such as crystalline cellulose, calcium carboxylmethyl cellulose and the like, emollients such as talc, magnesium stearate and the like, fluidity improvers such as light silicic acid anhydride, and the like.

Where solutions such as injections are employed in the parenteral preparations, they can be prepared using salts of the compounds of the invention. For instance, the hydrochloride of the compound No. 3 which is soluble in water or physiological salt solution can be made in the form of injections in usual manner.

The suppository can be made, for example, by dispersing compounds of the invention in ordinarily employed bases such as cacao butter, synthetic oils and fats as usual and solidifying the dispersion.

As will be understood from the foregoing, the compounds of the invention have been found to show improved antibody productivity and cellular immunity and stimulate the growth of the phagocytosis of mouse's splenic lymphocytes. It has been also found that the compounds contribute to accelerate the differentiation of myeloid cells into granulocytes and macrophages.

Accordingly, the compounds of the invention can be applied as drug against various diseases which will cause immunological abnormality or deficiency or diseases which will cause abnormality or deficiency in myeloid cells or differentiation thereof. In other words, the compounds of the invention are very useful as in improving drug against various infectious diseases based on bacterial or viral infection, nephritis, hepatitis, arthritis, rheumatoid, collagen disease, multiple sclerosis, systematic lupus erythematodes, immunopathy caused by drug, peripheral leucocytal abnormality or deficiency, and the like.

Examples for preparations are described.

EXAMPLE 1 (Tablet)

| | |
|---|---|
| Methyl 5-(4-carboxyphenyl)-2,3-dihydro-5H, 10bH-thiazolo[3,2-c][1,3]benzoxadine-3-carbonate (Compound No. 17) | 100 mg |
| D-Mannitol | 150 mg |
| Crystalline cellulose | 50 mg |
| Potato starch | 28 mg |
| Calcium carboxymethyl cellulose | 16 mg |
| Talc | 4 mg |
| Magnesium stearate | 2 mg |
| TOTAL | 350 mg |

The above ingredients are taken and formed into one tablet by usual manner.

EXAMPLE 2 (Capsule)

| | |
|---|---|
| Compound of No. 17 | 25 mg |
| Crystalline cellulose | 17 mg |
| Light silicic acid anhydride | 7 mg |
| Magnesium stearate | 1 mg |
| Lactose | 130 mg |
| TOTAL | 180 mg |

The above ingredients were used to make granules by usual manner and charged into a No. 3 capsule.

EXAMPLE 3 (Injection)

50 mg of 4-(2,3-dihydro-5H,10bH-thiazolo[3,2-c][1,3]benzoxadine-5-yl)benzaldehyde (Compound No. 3) hydrochloride was dissolved in physiological salt solution to make the total amount at 2 ml. By usual manner, the solution was subjected to the sterile filtration using a membrane filter, charged into a glass ampule and sealed by fusing to give an injection.

EXAMPLE 4 (Suppository)

| | |
|---|---|
| Compound of No. 3 | 50 mg |
| Cacao butter | 1,150 mg |
| TOTAL | 1,200 mg |

The above ingredients were molten and agitated by usual manner and molded and solidified to give one suppository.

What is claimed is:

1. A method of stimulating antibody producing cells in a host having immunological abnormality or deficiency, comprising:
administering to said host an antibody stimulating amount of a compound of the formula:

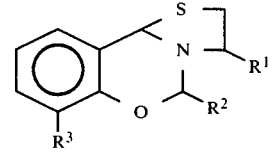

or salt thereof wherein $R^1$ is hydrogen, carboxy or lower alkoxycarbonyl; $R^2$ is phenyl, substituted phenyl, lower alkyl or furyl and $R^3$ is hydrogen or lower alkoxy.

2. The method of claim 1, wherein $R^2$ is a phenyl group which is substituted with at least one group selected from the group consisting of halogen, hydroxyl, carboxy, lower alkoxy, methylenedioxy, an aldehyde group, amino, nitro and a group of the formula:

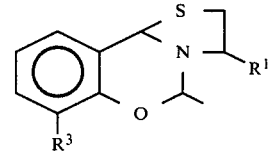

in which $R^1$ is hydrogen, carboxy, or lower alkoxycarbonyl and $R^3$ is hydrogen or lower alkoxy.

3. The method of claim 1, wherein $R^1$ is hydrogen, $R^2$ is 4-formylphenyl, and $R^3$ is hydrogen.

4. The method of claim 1, wherein said compound is prepared in a form suitable for oral administration.

5. The method of claim 1, wherein said compound is administered in an amount of 0.01–500 mg/kg.

6. The method of claim 1, wherein said compound is prepared in a form suitable for parenteral administration.

7. The method of claim 1, wherein said compound is administered in an amount of 0.005–250 mg/kg.

8. The method of claim 1, wherein said salt is soluble in water.

* * * * *